United States Patent
Rasolonjatovo et al.

(10) Patent No.: US 11,946,096 B2
(45) Date of Patent: *Apr. 2, 2024

(54) METHODS FOR ESTIMATING CLUSTER NUMBERS

(71) Applicant: ILLUMINA CAMBRIDGE LIMITED, Nr Saffron Walden (GB)

(72) Inventors: Isabelle Marie Julia Rasolonjatovo, Essex (GB); Jonathan Mark Boutell, Cambridge (GB); Vincent Peter Smith, Cambridge (GB); Roberto Rigatti, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 120 days.

This patent is subject to a terminal disclaimer.

(21) Appl. No.: 17/346,805

(22) Filed: Jun. 14, 2021

(65) Prior Publication Data

US 2022/0049288 A1 Feb. 17, 2022

Related U.S. Application Data

(63) Continuation of application No. 15/316,470, filed as application No. PCT/GB2015/051720 on Jun. 11, 2015, now Pat. No. 11,060,130.

(30) Foreign Application Priority Data

Jun. 11, 2014 (GB) ..................... 1410420

(51) Int. Cl.
*C12Q 1/68* (2018.01)
*C12Q 1/6806* (2018.01)
*C12Q 1/6818* (2018.01)
*C12Q 1/6837* (2018.01)
*C12Q 1/6874* (2018.01)

(52) U.S. Cl.
CPC ......... *C12Q 1/6806* (2013.01); *C12Q 1/6818* (2013.01); *C12Q 1/6837* (2013.01); *C12Q 1/6874* (2013.01)

(58) Field of Classification Search
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

| | | | |
|---|---|---|---|
| 5,130,238 A | 7/1992 | Malek | |
| 5,185,243 A | 2/1993 | Ullman | |
| 5,455,166 A | 10/1995 | Walker | |
| 5,573,907 A | 11/1996 | Carrino | |
| 5,679,524 A | 10/1997 | Nikiforov | |
| 6,214,587 B1 | 4/2001 | Dattagupta | |
| 7,115,400 B1 | 10/2006 | Adessi | |
| 7,582,420 B2 | 9/2009 | Oliphant | |
| 7,611,869 B2 | 11/2009 | Fan | |
| 7,670,810 B2 | 3/2010 | Gunderson | |
| 7,985,565 B2 | 7/2011 | Mayer | |
| 11,060,130 B2* | 7/2021 | Rasolonjatovo | C12Q 1/6874 |
| 2009/0226975 A1 | 9/2009 | Sabot et al. | |
| 2012/0109598 A1* | 5/2012 | Davey | C12Q 1/6874 703/2 |

FOREIGN PATENT DOCUMENTS

| | | |
|---|---|---|
| EP | 0 320 308 B1 | 6/1989 |
| EP | 0 439 182 B1 | 7/1991 |
| EP | 1912068 A | 4/2008 |
| WO | WO 1989/09835 | 10/1989 |
| WO | WO1989/10520 | 11/1989 |
| WO | WO 1989/12696 | 12/1989 |
| WO | WO 1990/01069 | 2/1990 |
| WO | WO 2002/084285 | 10/2002 |
| WO | WO 2005/065814 | 7/2005 |
| WO | WO2012/134602 | 10/2012 |

OTHER PUBLICATIONS

Bao et al., A Method for Evaluation of the Quality of DNA Microarray Spots; J Biochem Mol Biol. (2002) 35(5):532-535.
Kircher et al., Addressing Challenges in the Production and Analysis of Illumina Sequencing Data; BMC Genomics (2011) 12:382; 14 pages.
Krueger et al., Large Scale Loss of Data in Low-diversity Illumina Sequencing Libraries can be Recovered by Deferred Cluster Calling; PLoS One (2011) 6(1):e16607; 8 pages.
Weil et al., Toward a Universal Standard: Comparing Two Methods for Standardizing Spotted Microarray Data; Biotechniques (2002) 32(6):1310-1314.
Bronner, et al., Improved Protocols for Illumina Sequencing, Curr Protocols in Human Genetics, 18:18.2.1-18.2.42 (2014).
Dean et al., Comprehensive human genome amplification using multiple displacement amplificiation, Proc. Natl. Acad. Sci. USA 99:5261-66 (2002).
Grothues et al. PCR amplification of megabase DNA with tagged random primers (R-PCR), Nucleic Acids Res. 21(5):1321-2 (1993).
Lage et al., Whole genome analysis of genetic alterations in small DNA samples using hyperbranched strand displacement amplification and array—CGH, Genome Research 13:294-307 (2003).
Quail, et al., A large genome center's improvements to the Illumina sequencing system, Nature Methods 5(12):1005-1010 (2008).
Walker et al., Strand displacement amplification—an isothermal, in vitro DNA amplification technique, Nucl. Acids Res. 20(7):1691-96 (1992).

* cited by examiner

Primary Examiner — Frank W Lu
(74) Attorney, Agent, or Firm — Knobbe, Martens, Olson & Bear LLP

(57) ABSTRACT

The present invention relates to methods of imaging template hybridisation for estimating cluster numbers prior to solid phase amplification and sequencing. More particularly, an initial round of imaging is carried out at the single molecule template hybridisation stage which allows a general estimation of cluster numbers prior to clusters being formed. Amplification of the signal allows single molecule imaging to be carried out using standard sequencing imaging apparatus.

13 Claims, 6 Drawing Sheets

METHODS FOR ESTIMATING CLUSTER NUMBERS

The present invention relates to methods for estimating or predicting cluster numbers after solid phase amplification by imaging template hybridisation prior to solid phase amplification and sequencing. More particularly, an initial round of imaging of single molecules is carried out at the template hybridisation stage which allows a general estimation of cluster numbers to be predicted prior to clusters being formed. Amplification of the signal allows single molecule imaging to be carried out using standard sequencing imaging apparatus.

Next generation sequencing technology based on solid supports such as solid-phase DNA chips, e.g. Illumina's sequencing-by-synthesis (SBS) technology, is useful in allowing massively parallel sequencing allowing much more rapid and cost effective sequencing options for looking at variable sequences. The technology has a broad range of applications including in genomics, transcriptomics and epigenomics.

Illumina's sequencing by synthesis (SBS) technology uses four fluorescently-labelled nucleotides to sequence the tens of millions of clusters on the flow cell surface in parallel. During each sequencing cycle, a single labelled deoxynucleoside triphosphate (dNTP) is added to the nucleic acid chain. The dNTPs have a 3' azide block as well as the fluorescent label attached to the base. The 3' azide acts as a terminator, so after each dNTP incorporation, the fluorescent dye is imaged to identify the base and then both azide block and the fluorescent label are cleaved chemically to allow incorporation of the next nucleotide (the fluorescent label itself does not act as the terminator). Since all four reversible terminator-bound dNTPs (A, C, T, G) are present as single, separate molecules, natural competition minimizes incorporation bias. Base calls are made directly from signal intensity measurements during each cycle, which greatly reduces raw error rates compared to other technologies. The end result is highly accurate base-by-base sequencing that eliminates sequence-context specific errors, enabling robust base calling across the genome, including repetitive sequence regions and within homopolymers.

Notably, there are a number of different SBS technologies available. Illumina's SBS sequencing technology as described above uses four fluorescently labelled nucleotides, whilst other sequencing technologies can use fewer labels (i.e. 2-dye chemistry) or unlabelled dNTPs (e.g. 454, Ion torrent). Although the Illumina technology is exemplified herein a skilled person would understand that the technology could be adapted for use with such other sequencing technologies.

Libraries submitted for SBS will generally consist of a sequence of interest flanked on either side by adapter constructs. On each end, these adapter constructs have binding sites which allow the library fragment to attach to a solid support such as a flow cell surface. The constructs also contain several other primer binding sites. Often, prior to sequencing, the target DNA is tagged and fragmented. This can be done using Illumina's Nextera technology where tagging and fragmentation is carried out in a single step often referred to as tagmentation. Transposomes simultaneously fragment the DNA and add adapter sequences to the ends. The tagmented (tagged and fragmented) DNA is then amplified by limited cycle PCR which also add indexes and sequencing primer sequences required for cluster formation.

Before attachment to a flow cell, the library fragments are denatured. P5' and P7' regions of single-stranded library fragments anneal to their complementary oligonucleotides (oligos) which are immobilised on the flow cell surface. The flow cell oligos act as primers and a strand complementary to the library fragment is synthesized.

The original strand is washed away, leaving behind fragment copies that are covalently bonded to the flowcell surface Many-fold copies of each fragment are generated by bridge amplification, creating clusters. During cluster generation, sequencing templates are immobilised on a proprietary flow cell surface. Solid-phase amplification, known as bridge amplification creates approximately 1,000 identical copies of each single template molecule in close proximity (diameter of one micron or less). Because this process does not involve photolithography, mechanical spotting, or positioning of beads into wells, densities on the order of 100 million single-molecule clusters per square centimetre are achieved.

The P5 region is then cleaved, resulting in clusters containing fragments which are attached by the P7 region. The sequencing primer anneals to the end of the fragment, and begins the sequencing by synthesis process. Fluorescently labelled reversible terminator is imaged (via laser excitation) as each dNTP is added, and then cleaved to allow incorporation of the next base. Base calls are made directly from signal intensity measurements during each cycle Everything is then stripped from the template and dsDNA clusters are reformed via re-synthesis (cycles of bridge amplification). Then, P7 is cut instead of P5, resulting in fragments which are attached by the P5 region. The sequencing primer anneals and sequences the other end of the template.

As all four reversible terminator-bound dNTPs are present during each sequencing cycle, natural competition minimizes incorporation bias in standard cases.

SBS systems allow for a massive quantity of sequence reads in parallel. Deep sampling and uniform coverage is used to generate a consensus and ensure high confidence in determination of genetic differences. Deep sampling allows the use of weighted majority voting and statistical analysis, similar to conventional methods, to identify homozygotes and heterozygotes and to distinguish sequencing errors. Each raw read base has an assigned quality score so that the software can apply a weighting factor in calling differences and generating confidence scores.

Although such technologies have revolutionised sequencing when compared to the traditional Sanger and Maxam and Gilbert methods, one of the most significant current difficulties with the technology relates to the accurate quantification of libraries to enable prediction of cluster numbers. Inaccurate quantification leads to a number of problems. Underloading, which results in too few clusters, does not affect sequencing data but does result in data yield being lower than desired resulting in cost increases and inefficiencies in the system. Overloading however, which results in too many clusters, can compromise the quality of the sequences.

The present invention provides a method of imaging strands at the template hybridisation stage, enabling general prediction of cluster numbers and possible corrections in the cases of under loading and over loading of a flow cell or solid support.

In accordance with the present invention there is provided a method of predicting cluster numbers from solid phase amplification of nucleic acids comprising:

providing a solid support having a plurality of capture primers immobilised thereon;

providing template strands able to hybridise to at least some of said capture primers;

labelling the template strands or extensions thereof, if said strands are not already labelled;

detecting the signal from the labelled strands or extensions thereof; and analysing said detected signal to determine the number of single template strands present on the solid support;

estimating the number of clusters or the cluster density that will be obtained after cluster amplification of said template strands.

The term cluster relates to "colonies" of immobilized nucleic acid molecules where each cluster or colony is formed from a plurality of identical immobilized polynucleotide strands and a plurality of identical immobilized complementary polynucleotide strands that are created via cluster amplification.

Unlike in bulk fluorescence measured in a microarray type analysis the present method does not just detect a "level" of signal in the assay. The present invention is actually counting or calculating the discrete, single molecule based (but often amplified) events seen in the assay, and correlating this to predict the number of clusters that will be obtained after cluster amplification.

Preferably, the method includes amplifying the signal from the labels after labelling the template strand or extensions thereof. Although signal amplification would be used in many current sequencing instruments due to their imaging capabilities, signal amplification may not always be required. The use of a sequencing instrument or detector that is capable of detecting single molecules would not require the signal amplification step.

Preferably, the step of labelling the template strands or extensions thereof comprises hybridising a labelled oligonucleotide to the template strand.

Alternatively, the template strands may already be labelled, for example if a library that is already labelled is used. This may for example be a library with a biotin or a dye at the 5' end. It is also envisaged that when a library is made there could be a mixture of labelled and unlabelled oligonucleotides which would be useful when working at high densities as not every molecule would be detectable by imaging (for example only 10% or 1% of molecules could be detected and a correction factor could be applied, e.g. 10× or 100× to calculate the actual real density).

Preferably, said template strands each comprising at least one label binding site.

Optionally the label binding site is a sequencing primer site.

Preferably, the step of labelling the template strands or extensions thereof comprises hybridising said template strands to said capture probes in the presence of labelled oligonucleotides able to hybridise to the label binding sites.

Optionally, the method includes the step of extending the template primers.

Optionally, the step of labelling the template strands or extensions thereof comprises using labelled dNTP during the extension step.

Optionally, the step of labelling the template strands or extensions thereof comprises hybridising a labelled oligonucleotide to the extended template strand.

Preferably the solid support is a flow cell.

Preferably the capture primers comprise P5 and P7 oligonucleotides.

Preferably the template strands contain adapter sequences. Said adapter sequences are complementary to at least one of the capture primers and will hybridise thereto under appropriate conditions.

Optionally the sequencing primer site comprises a SBS3 or SBS12 sequence.

Preferably the labelled oligonucleotides are SBS3' or SBS12' labelled sequences.

Preferably the labelled oligonucleotides or dNTPs are labelled with biotin.

Preferably signal amplification occurs by exposing the solid support to dye labelled streptavidin.

Further amplification occurs by providing subsequent exposures to anti-avidin and dye labelled streptavidin.

Preferably subsequent exposures to anti-avidin and dye labelled streptavidin result in between 10 and 100 dye molecules per hybridised template strand.

The dye labelled streptavidin comprises a fluorescent dye. Exemplary dyes include commercially available dyes such as Cy3 or Cy5.

Preferably, the step of detecting the signal from the labelled strands or extensions thereof comprises obtaining an image.

Optionally, the imaging is carried out with a fluorescence microscope.

The imager should be able to generate an image where you can make out objects which are 1 to a few microns apart. It doesn't have to be as high resolution as our sequencing systems (which can resolve objects down to ~700 nm apart), but fairly close to this.

Preferably, the method comprises the step of analysing the image and providing an estimate or prediction of cluster numbers.

Optionally, in order to minimise the density of objects to analyse, a mix of labelled and un-labelled oligonucleotides may be used. For example 10% labelled oligonucleotides could be used where a user would then be expecting to pick up 10% of the strands in the assay. Then, 1000 spots in the assay would be equivalent to 10,000 clusters. This is determined by the mixture of labelled to un-labelled oligonucleotides used. In reality, small variations at the oligonucleotide mixing stage will give rise to some variability in the numbers obtained, so the exact true relation may need to be calibrated for each batch of oligonucleotides if greater accuracy is required.

If analysis suggests that the predicted cluster density or number of clusters is good, i.e. within a predetermined desired range, then a first extension is carried out to copy the molecules onto the flowcell surface, before standard cluster amplification and processing.

If analysis suggests that the predicted cluster density or number of clusters is too high i.e. above a predetermined desired range, the original molecules are removed (for example by washing with sodium hydroxide). Preferably hybridisation of the template strands is then carried out at a lower template concentration and an extension step is carried out to copy the molecules onto the flowcell surface, thus proceeding to standard cluster amplification and processing. A second imaging at the single molecule level is not required.

Alternatively, it is also envisaged that if analysis suggests that the predicted cluster density or number of clusters is too high i.e. above a predetermined desired range, only a portion or fraction of the original molecules can be removed from the solid support. A plurality of different removal oligonucleotides, preferably two different removal oligonucleotides, can be hybridized in different proportions to the template molecules. A proportion of the removal oligonucleotides create a restriction site and then a restriction digestion step is then carried out to selectively remove molecules with the restriction site. In one embodiment, a certain fraction of the molecules are removed by hybridizing two different sets of removal oligonucleotides, one which creates a restrictions site the other which does not create said restriction site, in different proportions. For example, the P5-SBS3 sequence already includes a BglII site for restriction digestion and this could be used as one of the removal oligonucleotides with the second group of removal oligonucleotides not having the BglII restriction site. Restriction digestion can then be carried out using BglII restriction endonuclease, with only the strands with the oligonucleotide with the BglII restriction site being digested and removed.

A further option if analysis suggests that the predicted cluster density or number of clusters is too high i.e. above a predetermined desired range, is that Exonuclease could be used, e.g. Exonuclease I. By selecting protective oligonucleotides that would bind to only a portion of the "free" end (typically the 3' end) of the surface bound library molecules then a portion of the library molecules are protected and the remaining molecules are digested and removed. The amount of protective oligonucleotide can be determined by titration if required. Additional protective oligonucleotides can also be used to protect any P5 or P7 primers that we do not wish to have removed from the surface, as they may be required for further clonal amplification steps.

If analysis suggests that the predicted cluster density is too low, the molecules which are already on the flowcell are extended, and then an additional hybridising step is carried out to hybridise additional template strands to said capture probes which are then also extended before proceeding to standard cluster amplification and processing. A second imaging at the single molecule level is not required after the additional hybridisation step.

Optionally, the method includes the step of carrying out a first extension of the template strands. The extension step may use a high fidelity DNA polymerase to assemble nucleotides provided in solution.

The extension step results in the labelled oligonucleotide and associated signal amplification molecules being removed. This is believed to be by displacement of the labelled oligonucleotides and associated amplification molecules.

Optionally the method includes the further step of performing solid phase amplification followed by sequencing. The solid phase amplification is preferably bridge amplification. Preferably the sequencing is sequencing by synthesis.

In order to provide a better understanding of the present invention, example methods of counting of clusters at the template hybridization stage and possible adjustment are described. This can be followed by sequencing, preferably sequencing by synthesis, for example using Illumina's MISEQ™, HISEQ™ 2000 or HISEQ™ 2500 platforms and examples of the methodology in use in an automated or semi automated platform are also provided. Reference is made to the following figures.

CLUSTER AMPLIFICATION

Figure 1:
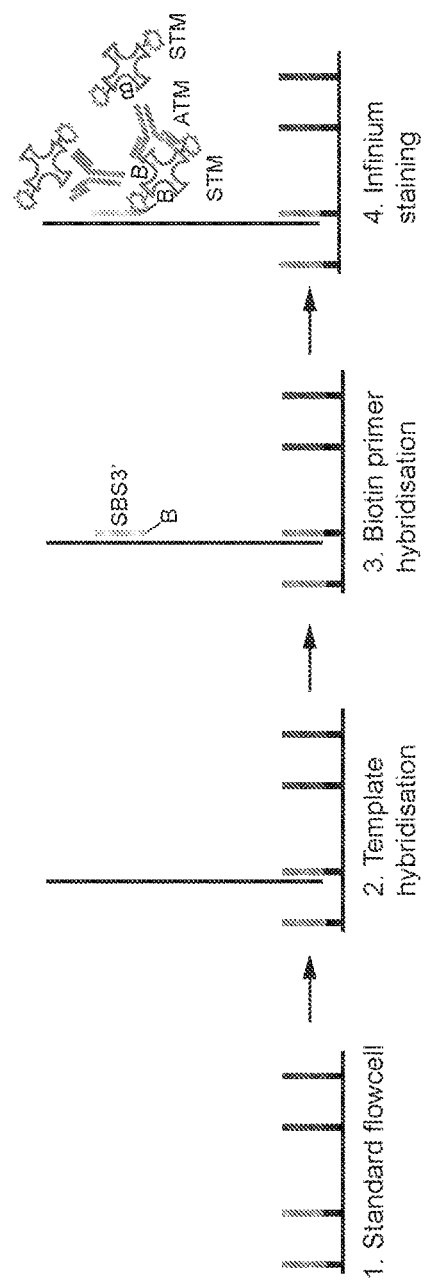
FIG. 1 is a basic schematic showing the steps of the method.

Standard cluster amplification methodologies are known in the art and are exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons.

It will be appreciated that any of the amplification methodologies described above or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized DNA fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, CA) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

The cluster counting methodology of the present invention allows a user to image template molecules hybridized to a solid support such as a flowcell surface prior to cluster amplification actually occurring. After analysis of the images, it should be possible to estimate how many clusters would be made if those molecules were taken on to sequencing. A decision can then be made as to how to process the flowcell. If the estimated density is within a desired range, then the molecules simply need to be 1st extended and amplified, for example using bridge amplification. If a lower density is desired, then the original molecules can be stripped off (dehybridized), and a lower concentration of template used to seed clusters. If a higher density is desired, then the original molecules can be 1st extended, and a second template mix used to increase the number of clusters made. In cases where the library concentration is very low it is possible to carry out additional rounds of hybridizing and extension as required. This will enable users to more reliably obtain required target cluster densities, so optimizing throughput on sequencing platforms and minimizing wastage and further improving the user experience.

Often, prior to sequencing, the target DNA is tagged and fragmented. This can be done using Illumina's Nextera technology where tagging and fragmentation is carried out in a single step often referred to as tagmentation. Transposomes simultaneously fragment the DNA and add adapter sequences to the ends. The tagmented (tagged and fragmented) DNA is then amplified by limited cycle PCR which also add indexes and sequencing primer sequences required for cluster formation.

In sequencing by synthesis (SBS) methods, libraries are constructed and, regardless of the library construction method, libraries submitted for SBS will generally consist of a sequence of interest flanked on either side by adapter constructs. On each end, these adapter constructs have flow cell binding sites which allow the library fragment to attach to a flow cell surface. The constructs also contain several other primer binding sites including sequencing binding sites e.g. SBS3/SBS12.

Before attachment to the flowcell, library fragments are denatured, and thus a single-stranded copy of the library fragment is copied by extension. The P5' and P7' regions of single-stranded library fragments anneal to their complementary oligonucleotides which are immobilised on the flowcell surface. Usually at this stage the flowcell oligonucleotides act as primers and a strand complementary to the library fragment is synthesized. The original strand is washed away, leaving behind fragment copies that are covalently attached to the flowcell surface and turned into a clonal population, for example many-fold copies of each fragment are generated by using bridge amplification. However, the present method allows the hybridised strands to be imaged or counted at the single molecule level, prior to cluster formation. It has surprisingly been found that this determination of the number of single molecule hybridised strands enables the general prediction of what cluster numbers will be obtained after bridge amplification thus allowing possible corrections to be made to ensure maximum use of the flow cell is achieved.

A basic overview of the methodology is shown in FIG. 1. Step 1 shows a standard flowcell on which a lawn of primers are covalently attached. Template strands are obtained as described above, and step 2 shows template strands being hybridised at one end to the lawn of primers on the flowcell under appropriate conditions. The hybridisation is carried out in the presence of biotinylated oligonucleotides which hybridise to sequencing primer sites at the other end of the template as can be seen in Step 3. In order to image the results it may be necessary to amplify the signal from each single bound molecule unless a sequencing platform is being used that is able to effectively image single molecules. Step 4 shows signal amplification using layers of infinium assay detection reagents that are flushed over to provide the signal amplification required to image with single molecule sensitivity on standard imaging platforms (e.g. Manteia™ microscope, MISEQ™). Current preferred methodology is to use 4 layers of dye-Streptavidin (STM) and 3 layers of anti-strep (ATM). This results in 10 to 100 dye molecules being associated with each single bound template molecule thus making it possible to image them using standard imaging equipment already used in sequencing technology. Once imaging is complete, the biotinylated oligonucleotides and signal amplification molecules can be removed. Flushing in normal extension enzymes can remove the labelled molecules.

STM=dye-labelled Streptavidin at 10 ug/ml in 1×B/W buffer (eg. B/W buffer recipe from MyOne beads protocol, Thermo)

ATM=biotinylated anti-Strep antibody at 1/100 dilution in XC3 buffer (Illumina Inc.)

Washes between layers of STM or ATM are with HT2 or PR2 (Illumina Inc). All STM/ATM and wash steps are performed at room temperature, incubations for 5 mins each.

Figure 2:
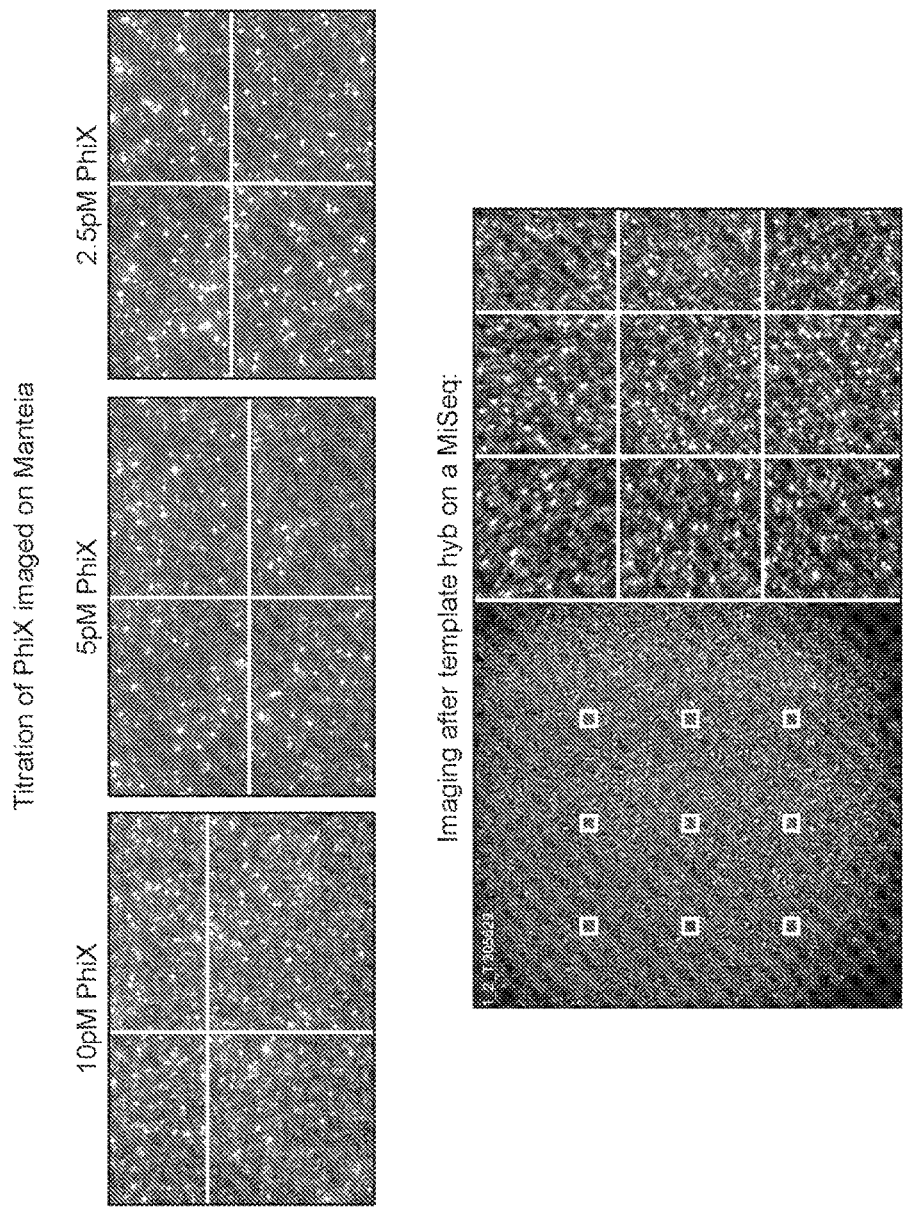
FIG. 2 is a number of images showing the results of imaging of single strands using a fluorescence microscope (top) or the MISEQ' imager (bottom)

FIG. 2 shows the results of imaging of single strands using the fluorescence microscope (top) or the MISEQ' imager (bottom) after carrying out the methodology of the present invention. PhiX™ was titrated and imaged and it can be seen that the single strands can be identified on the images.

Further work was then carried out where the final clusters were also imaged. The cluster image was overlaid against the images of the single strands and it was found that there was a correlation. It was noted that the number of single strands imaged correlated to within 10% to the number of clusters ultimately formed.

Figure 3:
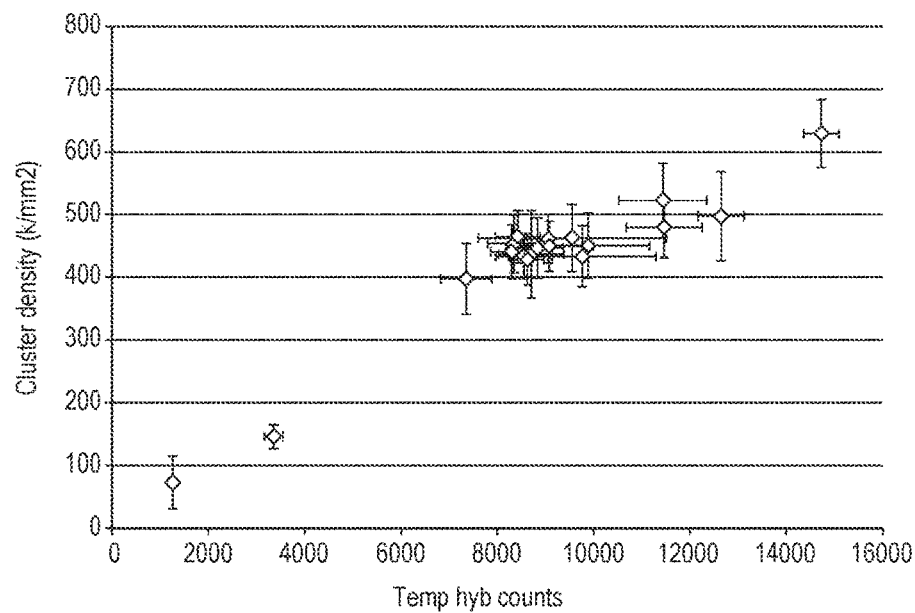
FIG. 3 shows a comparison of template hybridisation counts with cluster density for 14 standard TruSeq™ libraries.
Figure 4:
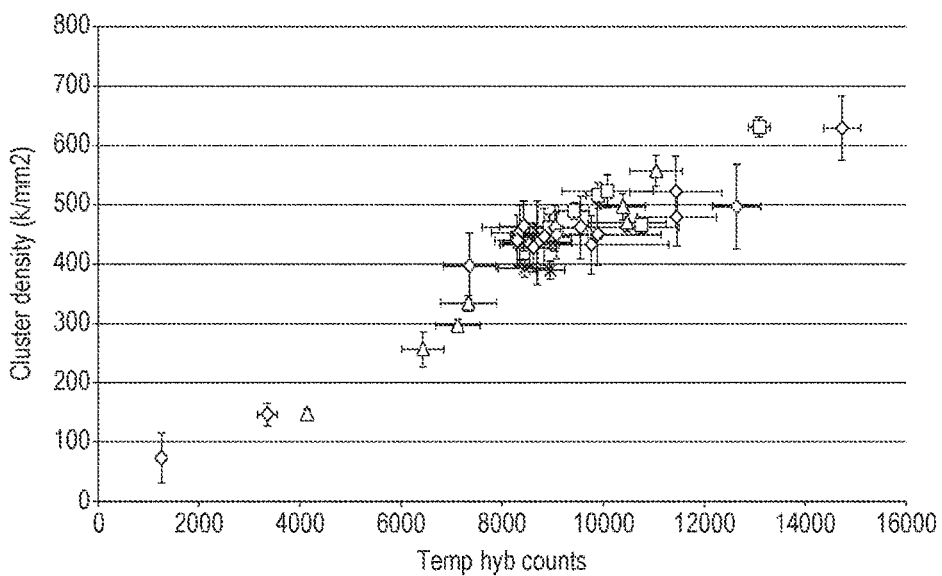
FIG. 4 shows a comparison of template hybridisation counts with cluster density for 14 standard TruSeq™ libraries and further incorporating 10 additional dual index libraries.

FIG. 3 shows a comparison of template hybridisation counts with cluster density for 14 standard TruSeq™ libraries including human, *B. cereus, E. coli* and *Rhodobacter*, from three different users. This showed a general correlation allowing general prediction of cluster numbers and thus an opportunity to correct underloading or overloading before progressing further. FIG. 4 shows a similar image further incorporating 10 additional dual index libraries. Again the general correlation can be seen. Testing of the 14 TruSeq™ and 10 dual index libraries (all SBS3/SBS12 format) shows good general correlation between the template hybridisation assay and cluster count as determined from the sequencing experiment. This allows detection of under- or over-loading events and correction with an accuracy of approximately +/−10%.

Once an estimate of cluster numbers has been obtained, a decision can be made as to whether correction of underloading or overloading is required. For example, a flowcell user would look for an optimum cluster density of 1 to 1.3 million clusters per mm2. If the estimated cluster density is within the desired range then a first extension is carried out to copy the molecules onto the flowcell surface, before standard cluster amplification and processing. If the estimated cluster density is too high, adjustment can be made by stripping off the original molecules (for example by washing with sodium hydroxide and rehybridizing at a lower template concentration. The system then proceeds to first extension to copy the molecules onto the flowcell surface, before standard cluster amplification and processing.

Figure 5:
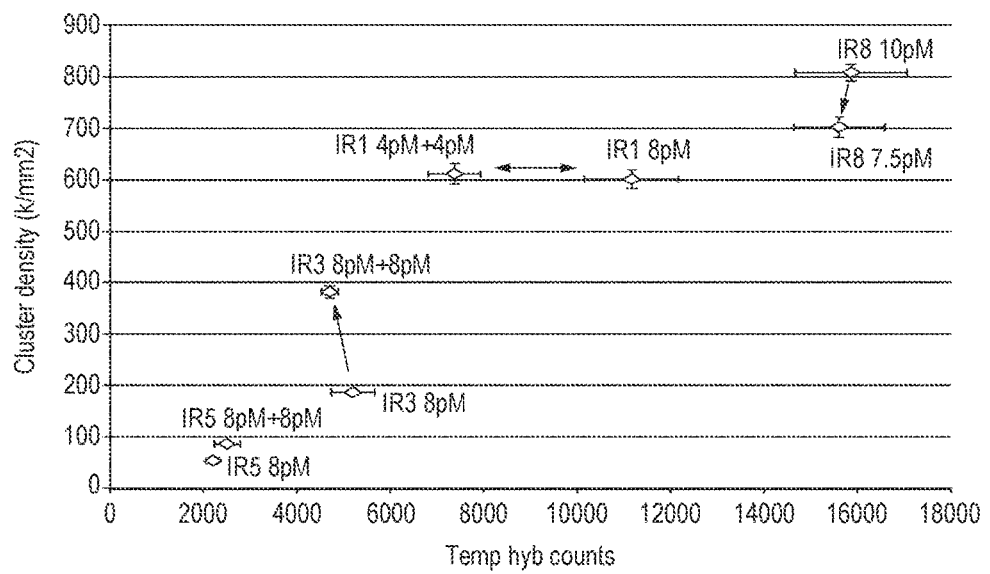
FIG. 5 shows the results for correcting under and overloading.
Figure 6:
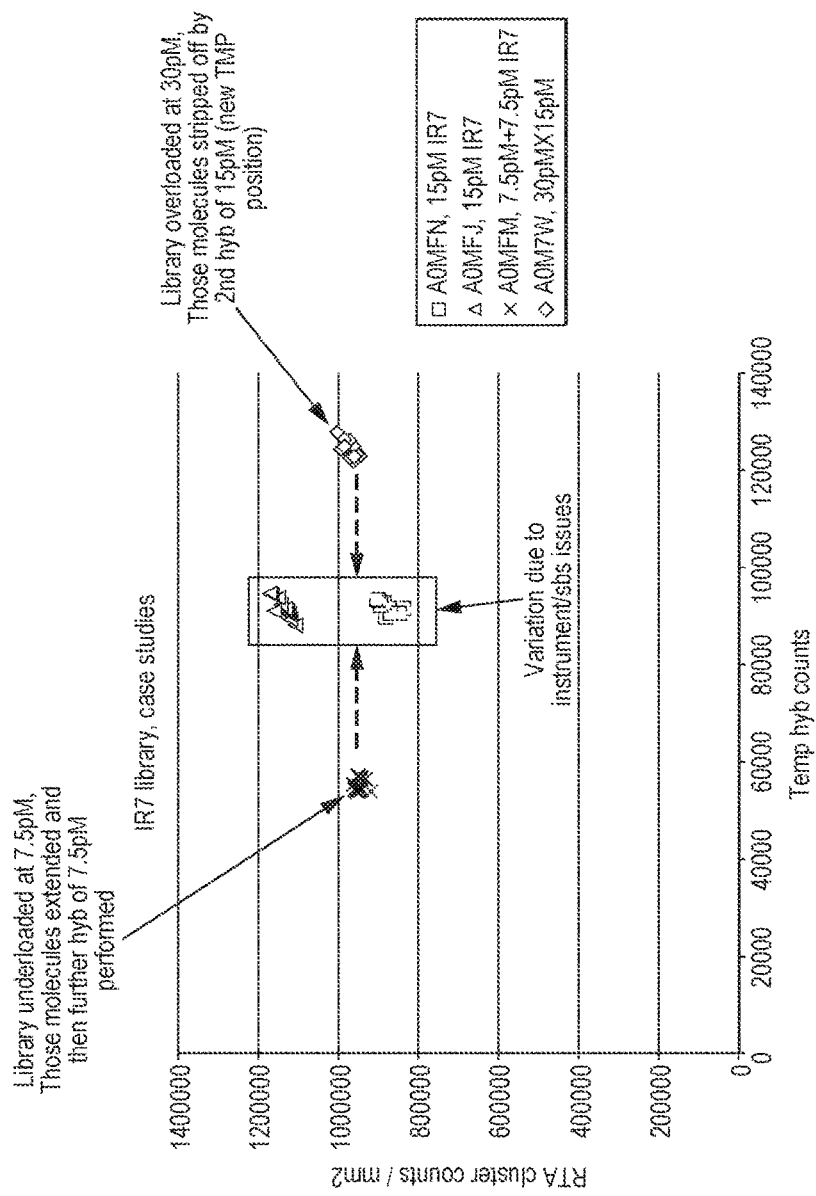
FIG. 6 shows the results of correcting underloading and overloading to give a preferred cluster density.

FIG. 5 shows the results for correcting under and overloading and it can be seen that after template hybridisation imaging, cluster numbers can be boosted by extending the 1st hybridised molecules, then hybridising a 2nd slug of template (e.g. IR3 8 pM+8 pM has twice as many clusters as IR3 8 pM) or reduced by not extending the imaged molecules, and then using a lower concentration of library for the 2nd hybridization (eg. IR8 used at 10 pM for a 1st hybridization, but then rehybridized at 7.5 pM—the 1st hybridized molecules are completely removed during the 2nd hyb event). FIG. 6 also shows the results of correcting underloading and overloading to give a preferred cluster density.

Examples of Methodology in Automated Platforms.

The methods are compatible with platforms which perform on-board cluster generation. This may require some amendment to the workflow of said platforms to allow additional movement between imaging stations and cluster formation stations as the method includes an additional imaging step prior to cluster formation when compared to current workflows.

When using MISEQ™, HISEQ™ or other automated systems it would be understood that appropriate control software/scripts would be required to automate the process e.g. to run the template hybridization imaging assay on the CBOT™, to enable single cycle scanning of the assay on the HISEQ™, and to enable cluster number adjustment on the CBOT™ etc. Software which enables counting of the molecules at the template hybridization stage may also be used. Due to the nature of the assay, these molecules only show up in a single image, which is different to the several images over several cycles which are typically used to identify clusters.

Signal amplification reagents are used to amplify the signal from the hybridised oligonucleotide templates and labelled primers. The signal amplification reagents include a dye labelled Streptavidin mix, anti-Strep antibody mix, and a modified hybridization buffer and can be used for the template hybridization imaging assay (see above for details on STM and ATM. The modified hybridization buffer is a Hybridization buffer with the labelled/unlabelled oligonucleotides each present at a concentration of 0.25 uM. Exemplary oligonucleotides are SBS3', SBS8', SBS12', NxtR1' and NxtR2').

A standard template hybridisation is carried out in the presence of labelled primers, in this case biotinylated oligonucleotides. Then the signal amplification is performed and layers of infinium assay detection reagents are flushed over the flowcell to provide the signal amplification required to image with single molecule sensitivity.

Scan mix can be flushed into the flowcell prior to imaging. The first read from the imager in a sequencing system such as MISEQ™ or HISEQ™ will scan the flowcell to image the hybridized molecules as a single cycle read.

An example protocol using MISEQ™ would be:
1. Thaw out MISEQ™ reagent cartridge in accordance with manufacturer's instructions, and also thaw out 1 tube each of STM (~5 mls), ATM (~5 mls) and modified Hyb buffer (~5 mls).
2. Pipette 750 ul STM (Template hyb imaging assay reagent, dye-labelled Streptavidin) into MISEQ™ cartridge position 18.
3. Pipette 750 ul ATM (Template hybridizaton imaging assay reagent, anti-Streptavidin) into MISEQ™ cartridge position 20.
4. Denature template according to the standard Illumin Inc. protocol for denaturing the template, except use the modified Hyb buffer (Hyb buffer+labeled sequencing primer complements) instead of Hyb buffer HT1 for denatured template dilution.
5. Pipette 600 ul of denatured template in modified Hyb buffer (TMP) into MISEQ™ cartridge position 17.
6. Run the single cycle TemplateImage run, following on-screen prompts on the MISEQ™.
7. At the end of the run the software will count the, or determine the number of the, objects seen in the images. Remaining steps are determined by the results of this analysis.

If it is determined that the estimated cluster density is within the desired range then a first extension is carried out to copy the molecules onto the flowcell surface, before standard cluster amplification and processing. Any standard combination of reads and index reads can be carried out at this stage.

If it is determined that the estimated cluster density is higher than the desired range, adjustment can be made by stripping off the original molecules and rehybridising at a lower template concentration. The system then proceeds to first extension to copy the molecules onto the flowcell surface, before standard cluster amplification and processing. Again, any standard combination of reads and index reads can be carried out at this stage. An example protocol using MISEQ™ would be:

8. Either dilute the denatured library to a lower concentration, or re-denature the library and dilute to a lower concentration in modified Hyb buffer.
9. Remove the reagent cartridge from the MISEQ™.
10. Pipette 600 ul of denatured template in modified Hyb buffer (TMP2) into MISEQ™ cartridge position 19.
11. Start another MISEQ™ run.

If it is determined that the estimated cluster density is lower than the desired range, adjustment can be made by extending the molecules which are already on the flowcell, and hybridising some more of that template. A first extension is carried out to copy the molecules onto the flowcell surface, followed by a template hybridisation. Then a second extension is carried out to copy the 2nd set of molecules onto the flowcell surface, before standard cluster amplification and processing. Again, any standard combination of reads and index reads can be carried out at this stage. An example protocol using MISEQ™ would be:

8. Either re-dilute the denatured library to a higher concentration, or re-denature the library and dilute to a higher concentration in modified Hyb buffer. Alternatively, it may be possible to use another aliquot of the diluted library at the same concentration as used for the TemplateImage run—this will need to be determined by the user.
9. Remove the reagent cartridge from the MISEQ™.
10. Pipette 600 ul of denatured template in modified Hyb buffer (TMP2) into MISEQ™ cartridge position 19.
11. Start another MISEQ™ run using the SampleSheet created in Step 17, following on-screen prompts.

Figure 7:
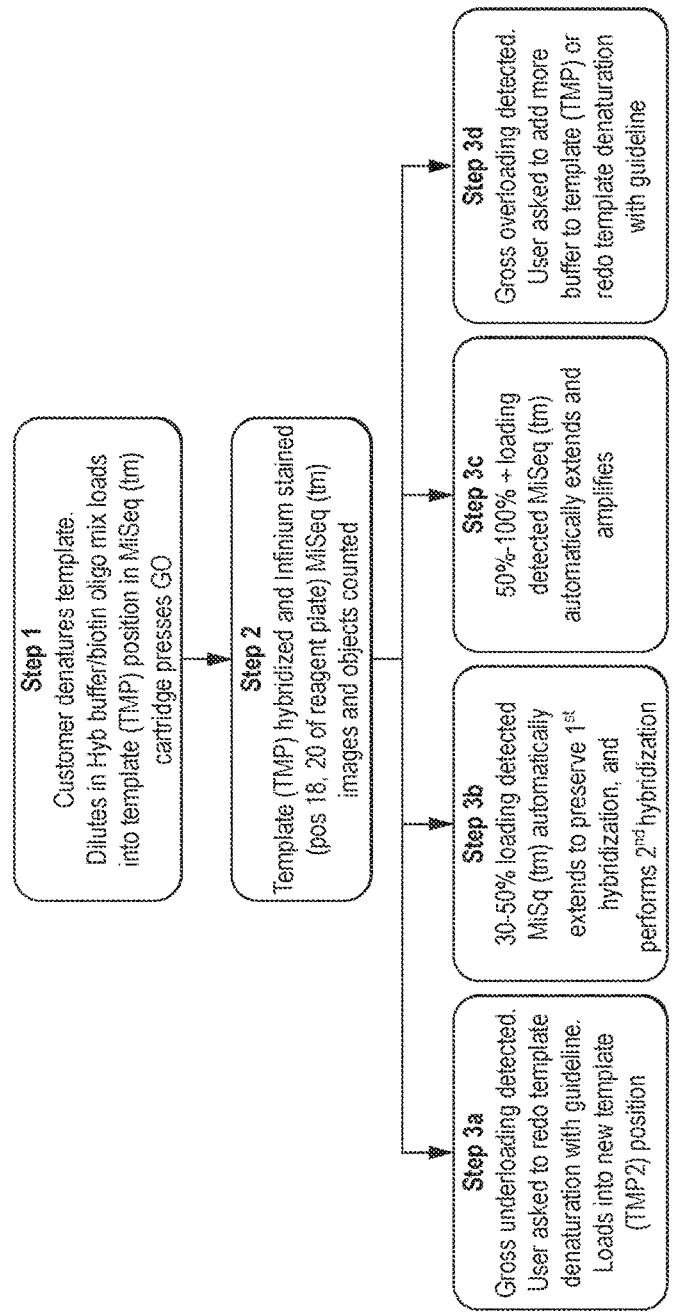
FIG. 7 is a sample workflow for an automated system such as MISEQ™.

FIG. 7 shows a possible workflow with Step 1, Step 3a and Step 3d being user action steps and the remaining steps being automated.

The methodology can also be carried out on other sequencing systems, for example the HISEQ™ 2000 system. The HISEQ™ 2000 workflow consists of 4 main steps:
1. Template hyb assay on the CBOT™
2. Imaging the template hyb assay on the HISEQ™
3. Cluster number adjustment (only carried out if the first determined cluster density is out with the desired range), amplification and read 1 prep on the CBOT'
4. Standard sequencing on the HISEQ™

1a. Copy relevant software scripts to the HISEQ™
1b. Thaw out 1 tube each of STM (~5 mls), ATM (~5 mls) and modified Hyb buffer (~5 mls).
1c. Pipette 600 ul of STM (Template hyb imaging assay reagent, dye-labelled Streptavidin) into each tube of a cBot reagent plate strip tube. Place this strip tube into plate position 2.
1d. Pipette 600 ul of ATM (Template hyb imaging assay reagent, anti-Streptavidin) into each tube of a CBOT™ reagent plate strip tube. Place this strip tube into plate position 4.
1e. Pipette 1000 ul of PR2 into each tube of 2 CBOT™ reagent plate strip tube. Place these into plate positions 1 and 3.

The CBOT™ plate layout is as described below:

| Row | Reagent | Label in Cluster kit | Volume (ul/well) |
|---|---|---|---|
| 1 | PR2 Wash | PR2 | 1000 |
| 2 | STM | STM | 600 |
| 3 | PR2 Wash | PR2 | 1000 |
| 4 | ATM | ATM | 600 |
| 5 | | | |
| 6 | | | |
| 7 | | | |
| 8 | | | |
| 9 | | | |
| 10 | | | |
| 11 | | | |
| 12 | | | |

1f. Denature template according to manufacturer's instructions e.g. in accordance with the Illumina Inc. manual using the modified Hyb buffer instead of Hyb buffer HT1 for denatured template dilution.
1g. Pipette 120 ul of denatured template in modified Hyb buffer 0.2 ml strip tubes (template tubes).
1h. Start a CBOT™ run using a HISEQ™ v3 flowcell, the reagent plate set up in steps 1b-1e, and the template mix strip tube set up in steps 1f-g.
1i. At the end of the run, the flowcell is ready to be scanned on the HISEQ™.
2a-d Set up imaging software.
2e. Thaw out HISEQ™ reagents.
2f. Start HISEQ™ run,
2g. Select required sequencing recipe.
2h. Select "Save All Images" from the drop down menu.
2i. Prime reagents through a dummy flowcell.
2j. Mount flowcell from step 1 onto the HISEQ™, and perform pump test.
2k. Start run.
2l. At the end of the run count the objects seen in the images (using steps 3a-3e).
3a. Thaw out a standard CBOT' reagent plate, and a tube of AMX (Amplification mix).
3b. Pipette 1 ml of PR2 into each tube of an empty CBOT™ reagent plate strip tube.
3c. Remove the HT1 strip tube (row 1) from the CBOT™ reagent plate and replace with the PR2 strip tube from step 3b.
3d. Pipette 1.3 mls of AMX (Amplification mix) into each tube of an empty CBOT reagent plate strip tube.
3e. Remove the HFE strip tube (row 2) from the cBot reagent plate and replace with the AMX strip tube from step 3d.
3f. For lanes requiring extension of the molecules on the flowcell, pipette 250 ul AMX into a CBOT reagent strip tube, to be placed into reagent plate position 12.
3g. For lanes requiring dehybing of the molecules on the flowcell, pipette 250 ul PR2 into the CBOT™ reagent strip tube, to be placed into reagent plate position 12.
3h. For lanes requiring a second hybridization of template, pipette 120 ul of template mix at the desired concentration in a 0.2 ml strip tube, to be placed into position 13.
3i. For lanes not requiring a second hybridization of template, pipette 120 ul of HT1 in a 0.2 ml strip tube, to be placed into position 13.

The cBot plate layout should be as described below:

| Row | Reagent | Label in Cluster kit | Volume (ul/well) |
|-----|---------|----------------------|------------------|
| 1 | PR2 Wash | PR2 | 1000 |
| 2 | Amp Mix | AMX | 1300 |
| 3 | Premix | LPM1 | 1150 |
| 4 | Amp Mix | LAM1 | 1150 |
| 5 | Formamide | LDR1 | 1150 |
| 6 | Amp Mix | LAM1 | 1150 |
| 7 | Wash Buffer | HT2 | 1000 |
| 8 | Linearization Mix | LMX1 | 300 |
| 9 | Blocking Mix | BMX | 350 |
| 10 | 0.1N NaOH | HP5 | 500 |
| 11 | Primer Mix | HP1 | 300 |
| 12 | Ext mix/Wash buffer | AMX/PR2 | 250 |

3j. Transfer the flowcell from the HISEQ™ back to the CBOT' and run using the reagent plate set up in steps 3a-3g, and the template mix strip tube set up in steps 3h-i.

3k. At the end of the run, the flowcell is ready to be sequenced on the HISEQ~ 2000.

4a. The fourth step of the HISEQ™ 2000 workflow is the same as setting up a standard HISEQ™ 2000 run, as the cluster numbers have been adjusted, amplified and processed on the CBOT™ in step 3.

4b. Restart HCS so that the scan settings are restored.

4c. Set up HISEQ™ 2000 run as normal.

The term "amplifying" as used herein is intended to mean the process of increasing the numbers of a template polynucleotide sequence by producing one or more copies. Accordingly it will be clear that the amplification process can be either exponential or linear. In exponential amplification the number of copies made of the template polynucleotide sequence increases at an exponential rate. For example, in an ideal PCR reaction with 30 cycles, 2 copies of template DNA will yield 230 or 1,073,741,824 copies. In linear amplification the number of copies made of the template polynucleotide sequences increases at a linear rate. For example, in an ideal 4-hour linear amplification reaction whose copying rate is 2000 copies per minute, one molecule of template DNA will yield 480,000 copies.

The term "immobilized" or "bound" as used herein is intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to a support under conditions in which it is intended to use the support, for example in applications requiring nucleic acid amplification and/or sequencing.

In many embodiments of the invention, amplification primers for solid phase amplification are immobilized by covalent attachment to a solid support at or near the 5' end of the primer, leaving the template-specific portion of the primer free to anneal to its cognate template and the 3' hydroxyl group free to function in primer extension. The chosen attachment chemistry will depend on the nature of the solid support, and any functionalization or derivitization applied to it. The primer itself may include a moiety, which may be a non-nucleotide chemical modification to facilitate attachment. In particular embodiments the primer may include a sulphur containing nucleophile such as phosphothioate or thiophosphate at the 5' end. In the case of solid supported polyacrylamide hydrogels, this nucleophile may bind to a bromoacetamide group present in the hydrogel. In a preferred embodiment the means of attaching the primers to the solid support is via 5' phosphothioate attachment to a hydrogel comprised of polymerised acrylamide and N-(5-bromoacetamidylpentyl) acrylamide (BRAPA). Such an arrangement is described more fully in co-pending application WO 05/065814, whose contents are incorporated herein by reference.

Single stranded template polynucleotide molecules may be attached to a solid support via hybridization to immobilized primers, or alternatively the single stranded polynucleotide molecules may also be directly attached to the solid support at or near the 5' end. The chosen attachment chemistry will depend on the nature of the solid support, and any functionalization or derivitization applied to it. The single stranded polynucleotide molecule itself may include a moiety, which may be a non-nucleotide chemical modification to facilitate attachment. In particular embodiments a single stranded polynucleotide molecule may include a sulphur containing nucleophile such as phosphorothioate or thiophosphate at the 5' end. In the case of solid supported polyacrylamide hydrogels, this nucleophile can also bind to the bromoacetamide groups present in the hydrogel. In one embodiment the means of attaching the single stranded polynucleotide molecule to the solid support is via 5' phosphorothioate attachment to a hydrogel comprised of polymerised acrylamide and N-(5-bromoacetamidylpentyl) acrylamide (BRAPA). Such an arrangement is described more fully in co-pending application WO 05/065814, whose contents are incorporated herein by reference.

The term "solid support" as used herein refers to any surface, inert substrate or matrix to which nucleic acids can be attached such as, for example, beads, including latex or dextran beads, a surface, such as a polystyrene or polypropylene surface, polyacrylamide gel, gold surfaces, glass surfaces and silicon wafers. The solid support may be a glass surface. The solid support may be a planar surface, although the invention also works on beads which are moved between containers of different buffers, or beads arrayed on a planar surface. The solid support can be a flow cell, resin, gel, bead, well, column, chip, membrane, matrix, plate or filter.

In certain embodiments the solid support may comprise an inert substrate or matrix which has been "functionalized", for example by the application of a layer or coating of an intermediate material comprising reactive groups which permit covalent attachment to molecules such as polynucleotides. By way of non-limiting example such supports may include polyacrylamide hydrogels supported on an inert substrate such as glass. In such embodiments the molecules (e.g. polynucleotides) may be directly covalently attached to the intermediate material (e.g. the hydrogel) but the intermediate material may itself be non-covalently attached to the substrate or matrix (e.g. the glass substrate). Such an arrangement is described more fully in co-pending application WO 05/065814, whose contents are included herein by reference.

Primer oligonucleotides or primers are polynucleotide sequences that are capable of annealing specifically to one or more single stranded polynucleotide template to be amplified under conditions encountered in the primer annealing step of each cycle of an amplification reaction. Generally amplification reactions can use at least two amplification primers, often denoted "forward" and "reverse" primers. In certain embodiments the forward and reverse primers may be identical. The forward primer oligonucleotides can include a "template-specific portion", being a sequence of nucleotides capable of annealing to a primer-binding sequence in at least one strand of the molecule to be amplified. Reverse primer oligonucleotides can include a template specific portion capable of annealing to the complement of the strand to which the forward primer anneals during the annealing step. Generally primer oligonucleotides are single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, again provided that such modifications do not permanently prevent primer function. Chemical modifications may, for example, facilitate covalent attachment of the primer to a solid support. Certain chemical modifications may themselves improve the function of the molecule as a primer, or may provide some other useful functionality, such as providing a site for cleavage to enable the primer (or an extended polynucleotide strand derived therefrom) to be cleaved from a solid support.

"Solid-phase amplification" as used herein refers to any nucleic acid amplification reaction carried out on or in association with a solid support such that all or a portion of the amplified products are immobilized on the solid support. In particular, the term encompasses solid phase amplification reactions analogous to standard solution phase PCR except that one or both of the forward and reverse amplification primers is/are immobilized on the solid support.

In solid phase amplification, suitable conditions can be applied to a single stranded polynucleotide molecule and a plurality of immobilized primer oligonucleotides such that sequence Z at the 3' end of the single stranded polynucleotide molecule hybridizes to a primer oligonucleotide sequence X to form a complex wherein, the primer oligonucleotide hybridizes to the single stranded template to create a "bridge" structure. Suitable conditions such as neutralizing and/or hybridizing buffers are well known in the art (See Sambrook et al., Molecular Cloning, A Laboratory Manual, 3rd Ed, Cold Spring Harbor Laboratory Press, NY; Current Protocols, eds Ausubel et al.). The neutralizing and/or hybridizing buffer may then be removed. One suitable hybridization buffer is referred to as "amplification pre-mix", and contains 2 M Betaine, 20 mM Tris, 10 mM Ammonium Sulfate, 2 mM Magnesium sulfate, 0.1% Triton™, 1.3% DMSO, pH 8.8.

By applying suitable conditions, an extension reaction can be performed for a complex formed between immobilized primer and single stranded polynucleotide template. The primer oligonucleotide of the complex can be extended by sequential addition of nucleotides to generate an extension product complementary to the single stranded polynucleotide molecule.

Examples of enzymes with polymerase activity which can be used in the present invention are DNA polymerase (Klenow fragment, T4 DNA polymerase, Bst polymerase), heat-stable DNA polymerases from a variety of thermostable bacteria (such as Taq, VENT, Pfu, Tfl, Phusion DNA polymerases) as well as their genetically modified derivatives (TaqGold, VENTexo, Pfu exo). A combination of RNA polymerase and reverse transcriptase can also be used to generate the extension products. A useful polymerase enzyme can have strand displacement activity. The polymerase enzyme can be active at a pH of about 7 to about 9, particularly pH 7.9 to pH 8.8. The nucleoside triphosphate molecules used can be deoxyribonucleotide triphosphates, for example dATP, dTTP, dCTP, dGTP, or they can be ribonucleoside triphosphates for example ATP, UTP, CTP, GTP. The nucleoside triphosphate molecules may be naturally or non-naturally occurring. An amplification reaction may also contain additives such as DMSO and or Betaine, for example, to normalise the melting temperatures of the different sequences in the template strands. A suitable solution for initial cycles of extension is referred to as "amplification mix" and contains 2 M betaine, 20 mM Tris, 10 mM Ammonium Sulfate, 2 mM Magnesium sulfate, 0.1% Triton™, 1.3% DMSO, pH 8.8 plus 200 mM dNTPs and 80 units/mL of Bst polymerase (e.g. NEB Product ref M0275L).

The denaturation can be carried out using heat or by using a denaturing buffer. Suitable denaturing buffers are well known in the art (See Sambrook et al., Molecular Cloning, A Laboratory Manual, 3rd Ed, Cold Spring Harbor Laboratory Press, NY; Current Protocols, eds. Ausubel et al.). By way of example it is known that alterations in pH and low ionic strength solutions can denature nucleic acids at substantially isothermal temperatures. Formamide and urea can be used for denaturation. In a particular embodiment the concentration of formamide is 50% or more, and may be used neat. Such conditions result in denaturation of double stranded nucleic acid molecules to single stranded nucleic acid molecules. Alternatively or additionally, the strands may be separated by treatment with a solution of very low salt (for example less than 0.1 mM cationic conditions) and high pH (>12) or by using a chaotropic salt (e.g. guanidinium hydrochloride). In a particular embodiment, a strong base may be used. A strong base is a basic chemical compound that is able to deprotonate very weak acids in an acid base reaction. The strength of a base is indicated by its pKb value. Compounds with a pKb value of less than about 1 are called strong bases and are well known to a skilled practitioner. In a particular embodiment the strong base is Sodium Hydroxide (NaOH) solution used at a concentration of from 0.05 M to 0.25 M. More particularly NaOH is used at a concentration of 0.1 M.

It may be advantageous to perform optional washing steps in between steps of an amplification method. For example, an extension buffer without polymerase enzyme with or without dNTPs could be applied to a solid support upon which amplification is being carried out and it can be applied before being removed and replaced with complete extension buffer (extension buffer that includes all necessary components for extension to proceed).

Multiple cycles of amplification on a solid surface under conditions exemplified above can result in a nucleic acid colony or "cluster" comprising multiple immobilized copies of a particular single stranded polynucleotide sequence and its complementary sequence. Initial immobilization of a single stranded polynucleotide molecule under conditions exemplified herein can result in the single stranded polynucleotide molecule only hybridizing with primer oligonucleotides located at a distance within the total length of the single stranded polynucleotide molecule. Thus, the boundary of the nucleic acid colony or cluster formed can be limited to a relatively local area, namely the area in which the initial single stranded polynucleotide molecule was immobilized. If conditions are used wherein the templates and the complementary copies thereof remain immobilized throughout the whole amplification process, then the templates do not become intermingled other than by becoming large enough to overlap on the surface. In particular embodiments, there is no non-immobilized nucleic acid during any part of the amplification process, and thus the templates cannot diffuse and initiate further clusters elsewhere on the surface.

An amplification process may entail cycles of exposure to conditions for hybridization, extension and denaturation of nucleic acid sequences. The cycles may be repeated in order to obtain a sufficient level of amplification. The amplification process (e.g., in a round) may be carried using, for example, 10, 15, 20, 25, 30, 35, 40 or 45 or more cycles of amplification. Each cycle may be carried out using the same reagents and conditions, or the reagents and/or conditions may be varied between different cycles. For example, the first 5, 10, 15, 20 or 25 cycles, in a first round, may be carried out using extension conditions with equimolar concentrations of four different nucleotide types, and subsequent cycles, in a second round, may be carried out using conditions resulting in less efficiently incorporated nucleotides. Normalized amplification conditions using less efficiently incorporated nucleotides can be used. An increased number of amplification cycles can be carried out, as the overall efficiency of amplification is reduced, and the AT rich sequences do not become over-amplified. It is therefore possible to carry out, for example, 25 cycles of amplification in a first round using equimolar nucleotide concentrations, and 15 or more additional cycles of amplification in a second round using conditions using nucleotides incorporated with lower efficiency (for example limited concentrations of A and/or T nucleotides). Such additional cycles in the second round amplify the GC rich clusters preferentially to the AT rich clusters, hence normalizing the intensity of clusters of different sequence compositions.

Hybridization, extension and denaturation steps of an amplification method set forth herein may all be carried out at the same, substantially isothermal temperature. Preferably the temperature is from 37° C. to about 75° C., depending on the choice of enzyme, more preferably from 50° C. to 70° C., yet more preferably from 60° C. to 65° C. for Bst polymerase. In a particular embodiment the substantially isothermal temperature may be around the melting temperature of the oligonucleotide primer(s). Methods of calculating appropriate melting temperatures are known in the art. For example the annealing temperature may be about 5° C. below the melting temperature (Tm) of the oligonucleotide primers. In yet another particular embodiment the substantially isothermal temperature may be determined empirically. The temperature can be that at which the oligonucleotide displays greatest specificity for the primer binding site whilst reducing non-specific binding. Although the above information is exemplary of an isothermal method, one skilled in the art would understand that the hybridization, extension and denaturation steps of amplification are performed at different temperatures depending on the sequencing instrument that is being used.

Although embodiments above describe detection of fluorescent signals from individual strands, the detection doesn't necessarily have to count the individual molecules e.g. a Typhoon scanner could be used to capture a bulk fluorescent signal—so long as the correlation can be made between this signal and final cluster number, then the method would still work. Further, the detection doesn't have to be fluorescence based or indeed optical—e.g. we could use HRP type signal amp cascades and detect signal by chemiluminescence, or use some type of cascade which generates H+ ions and detect pH changes

What is claimed is:

1. A method of preparing a first solid support for bridge amplifications of template strands of nucleic acids, comprising:
   (a) predicting numbers of clusters or cluster densities on a first solid support, comprising:
      (i) providing the first solid support, wherein a plurality of capture primers is immobilised on the first solid support;
      (ii) hybridizing template strands of nucleic acids to at least some of said capture primers, thereby forming hybridized template strands;
      (iii) obtaining labelled template strands by labelling the hybridized template;
      (iv) determining the number of hybridized template strands present on the first solid support by counting images on the first solid support generated by detectable signals produced from the labelled template strands; and
      (v) correlating the number of hybridized template strands present on the first solid support to a number of hybridized reference template strands present in a reference, thereby obtaining the predicted number of clusters or predicted cluster densities on the first solid support,
   wherein the reference is a standard curve produced by plotting different numbers of the hybridized reference template strands present on a second solid support versus different numbers or densities of clusters on the second solid support generated by bridge amplifications of the different numbers of the hybridized reference template strands present on the second solid support;
   (b) comparing the predicted number of clusters or predicted cluster densities with an optimum range of clusters or optimum cluster density expected to be obtained on the first solid support if bridge amplifications of the hybridized template strands are performed on the first solid support; and
   (c) preparing the first solid support for the bridge amplifications of the template strands of the nucleic acids by adjusting the amounts of the hybridized template strands on the first solid support based on a result from step (b), wherein the adjusting step comprises
      (i) removing at least a fraction of the hybridized template strands from the first solid support if the predicted number of clusters or predicted cluster densities is greater than the optimum range of clusters or optimum cluster density expected to be obtained on the first solid support or
      (ii) hybridizing a further amount of the template strands of the nucleic acids to at least some of the capture primers unhybridized to the template strands of the nucleic acids on the first solid support if the predicted number of clusters or predicted cluster densities is lower than the optimum range of clusters or optimum cluster density expected to be obtained on the first solid support.

2. The method of claim 1, further comprising extending the capture primers hybridized to the template strands of the nucleic acid if the predicted number of clusters or predicted cluster densities is within the optimum range of clusters or optimum cluster density expected to be obtained on the first solid support.

3. The method of claim 2, further comprising performing a solid phase amplification of the hybridized template strands.

4. The method of claim 3, wherein the solid phase amplification is a bridge amplification.

5. The method of claim 2, further comprising sequencing amplified products generated from the hybridized template strands.

6. The method of claim 1, wherein the predicted number of clusters or predicted cluster densities is greater than the optimum range of clusters or optimum cluster density expected to be obtained on the first solid support.

7. The method of claim 6, wherein said removing at least a fraction of the hybridized template strands from the first solid support comprises washing the hybridized template strands from the first solid support with sodium hydroxide.

8. The method of claim 6, wherein said removing at least a fraction of the hybridized template strands from the first solid support comprises digesting the hybridized template strands from the first solid support with an enzyme.

9. The method of claim 6, further comprising producing double-stranded polynucleotides by hybridizing a plurality of removal oligonucleotides to at least a portion of the hybridized template strands, wherein the double-stranded polynucleotides comprises a restriction enzyme site; and contacting the double-stranded polynucleotides with a restriction enzyme.

10. The method of claim 6, further comprising producing protected double-stranded polynucleotides by hybridizing a plurality of protective oligonucleotides to at least a portion of the hybridized template strands.

11. The method of claim 10, further comprising contacting the hybridized template strands with an endonuclease capable of digesting single-stranded nucleic acids.

12. The method of claim 6, further comprising hybridizing the template strands of the nucleic acids to at least some of the capture primers at a lower temperature.

13. The method of claim 1, wherein the predicted number of clusters or predicted cluster densities is lower than the optimum range of clusters or optimum cluster density expected to be obtained on the first solid support.

* * * * *